(12) United States Patent
Ström

(10) Patent No.: US 6,679,258 B1
(45) Date of Patent: Jan. 20, 2004

(54) VENTILATOR OPERABLE IN A COMPENSATED VOLUME SUPPORT MODE

(75) Inventor: Christer Ström, Pitea (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/377,847

(22) Filed: Aug. 20, 1999

(30) Foreign Application Priority Data

Aug. 25, 1998 (SE) ............................................. 9802827

(51) Int. Cl.[7] ............................................. A61M 16/00
(52) U.S. Cl. ............................. 128/204.21; 128/204.23; 128/204.18
(58) Field of Search ...................... 128/204.18, 204.21, 128/204.23, 204.22

(56) References Cited

U.S. PATENT DOCUMENTS

| | | | |
|---|---|---|---|
| 3,834,381 A | | 9/1974 | Peterson |
| 3,923,056 A | | 12/1975 | Bingmann et al. |
| 5,107,830 A | * | 4/1992 | Younes ................. 128/204.18 |
| 5,572,993 A | * | 11/1996 | Kurome et al. ......... 128/204.23 |
| 5,660,171 A | | 8/1997 | Kimm et al. |
| 5,743,253 A | * | 4/1998 | Castor et al. ........... 128/200.24 |
| 5,752,506 A | * | 5/1998 | Richardson ............ 128/204.18 |
| 5,765,558 A | * | 6/1998 | Psaros et al. .......... 128/207.14 |
| 5,782,233 A | * | 7/1998 | Niemi et al. ............ 128/202.22 |
| 5,878,744 A | * | 3/1999 | Pfeiffer ................. 128/204.23 |
| 5,884,622 A | * | 3/1999 | Younes .................. 128/204.21 |
| 5,934,274 A | * | 8/1999 | Merrick et al. ......... 128/203.25 |
| 5,957,130 A | * | 9/1999 | Krahbichler et al. ... 128/205.14 |
| 6,105,575 A | * | 8/2000 | Estes et al. ............ 128/204.23 |
| 6,135,105 A | * | 10/2000 | Lampotang et al. ... 128/204.18 |
| 6,196,222 B1 | * | 3/2001 | Heinonen et al. ....... 128/204.18 |
| 6,257,234 B1 | * | 7/2001 | Sun ....................... 128/204.18 |

FOREIGN PATENT DOCUMENTS

| | | |
|---|---|---|
| EP | 0 046 570 | 3/1982 |
| EP | 0 774 269 | 5/1997 |
| EP | 0 776 672 | 6/1997 |
| WO | WO 92/11054 | 7/1992 |
| WO | WO 97/22377 | 6/1997 |

* cited by examiner

Primary Examiner—Weilun Lo
Assistant Examiner—Mital Patel
(74) Attorney, Agent, or Firm—Schiff Hardin & Waite

(57) ABSTRACT

A ventilator for connection to a patient to provide assisted breathing, has a gas flow generator, a pressure meter, a flow meter and a control unit, which determines a gas pressure, on the basis of a pre-set tidal volume for the patient and measurement signals from the pressure meter and flow meter, for each breath and which regulates the gas flow generator so that it generates the determined gas pressure. An improved breathing mode, better tailored to the patient, is achieved by the control unit also determining the gas pressure to be generated by the gas flow generator on the basis of mechanical resistances and a variable corresponding to the aggregate effect of the resistance and elastance of the lungs.

10 Claims, 2 Drawing Sheets

VENTILATOR OPERABLE IN A COMPENSATED VOLUME SUPPORT MODE

BACKGROUND OF THE INVENTION

1. Field of the Invention

The present invention relates to a ventilator designated to provide assisted breathing to a patient and is of the type having a gas flow generator, a pressure meter, a flow meter, and a control unit which determines a gas pressure on the basis of a preset tidal volume for the patient and measurement signals from the pressure meter and the flow meter, for each breathing cycle, and which regulates the gas flow generator to generate the determined gas pressure.

2. Description of the Prior Art

Assisted breathing is provided for patients retaining at least some ability to breathe spontaneously. Ideally, assisted breathing should eliminate needless breathing effort by the patient, be adaptable to any changes in the patient's condition, contribute to the provision of good ventilation, especially in respect to the $CO_2$ level, and remain stable, despite any changes in the interface between the patient and the ventilator.

The resistance and elasticity of tubing and the patient's airways (including the lungs) all affect assisted breathing and the patient's own breathing efforts. Since these parameters change, e.g. when the patient shift/position, when the patient's condition improves or worsens etc., assisted breathing cannot be regarded as a constant function of the gas supplied in each breath.

Volume support breathing (VS) is one respiratory mode developed to supply assisted breathing. It is described, in principle, in FIG. 1. In VS the physician sets a target tidal volume to be achieved in each breath. When a spontaneous breath is detected, the ventilator imposes a first inspiration 2 of breathing gas, at a first positive pressure 4, on the patient. The volume of inspired gas is determined by measuring the flow 6 in the first inspiration 2 and integrating it over time. If the determined volume of gas does not correspond to the preset tidal volume, the next inspiration 8 is imposed at a second positive pressure 10 higher than in the first inspiration 2. The inspired volume is determined by measuring the flow 12. A third inspiration 14 is imposed at a third, even higher, positive pressure 16, and measurement of flow 18 will show that the inspired volume exceeds the target volume (in this example). Then a fourth inspiration 20 is imposed at a fourth positive pressure 22 lower than the third positive pressure 16. The resulting flow 24 produces a tidal volume in agreement With the preset value.

Pressure limitations, an apnea alarm, switching to the controlled mode if apnea occurs etc. are other functions in this operating mode, which contribute to good patient safety. Even though this mode is effective and is frequently used by physicians, it still has room for improvement, especially since it does not take into account nor adapt in an optimal fashion to, e.g. changes in airway and equipment elasticity and resistance.

Proportional assisted ventilation (PAV) is another breathing mode. This mode strives to provide assisted breathing adapted to the patient's breathing. In simple terms, this mode can be said to provide breathing assistance proportional to the patient's attempts at breathing. The proportion can be e.g. 1:3. In PAV, the patient's elastance is viewed as a constant, and the tidal volume varies with (and is related to) the patient's efforts.

The main disadvantages of PAV are that changes in the patient's condition are not taken into account, and the regulatory system is based on positive feedback, thereby making the system unstable. Therefore, this mode demands almost constant attendance of a doctor by the ventilator to adjust ventilator settings.

Automatic tube compensation (ATC) is a third known breathing mode. This is actually not a mode in itself but a way to compensate for the breathing resistance that develops in a tracheal tube with which the patient is connected to the ventilator. When compensation is provided for the tracheal tube's resistance, the patient should be able to breathe as if no tracheal tube were present. (For a layman, spontaneous breathing through a tracheal tube can be likened to breathing through a straw. Such breathing is very hard on a patient with a diseased or damaged lung.)

None of the breathing modes provides simultaneous adaptation to variations in the patient's intrinsic breathing or a predictable level of $CO_2$.

SUMMARY OF THE INVENTION

An object of the present invention is to provide a ventilator capable of generating a breathing mode that resolves the aforementioned problems.

The above object is achieved in accordance with the principles of the present invention in a ventilator of the type initially described, wherein the control unit determines the gas pressure which is to be generated by the gas flow generator on the basis of mechanical resistances "seen" by the ventilator and/or on the basis of a variable corresponding to the aggregate effect of the resistance and elasticity of the lungs of the patient.

When appropriate parts of known breathing modes are combined and these are combined with new components, a breathing mode is achieved with the advantages of other breathing modes but without their disadvantages. The new breathing mode regards e.g. the patient's elasticity and resistance as a variable (aggregated into a kind of impedance). As in VS, a physician sets a target for tidal volume, but the ventilator in the new breathing mode compensates for resistance in the ventilator system (primarily in the tracheal tube) and/or for variations in the patient's "impedance", which can be a result of improvement in or worsening of the patient's condition. The inventive breathing mode therefore can be referred to as "compensated volume support" (CVS).

In contrast to conventional volume support, VS, the pressure level can be controlled during the inspiration phase of CVS. Each breath will then result in a supplied tidal volume corresponding to the selected tidal volume.

DESCRIPTION OF THE PREFERRED EMBODIMENTS

Figure 1:
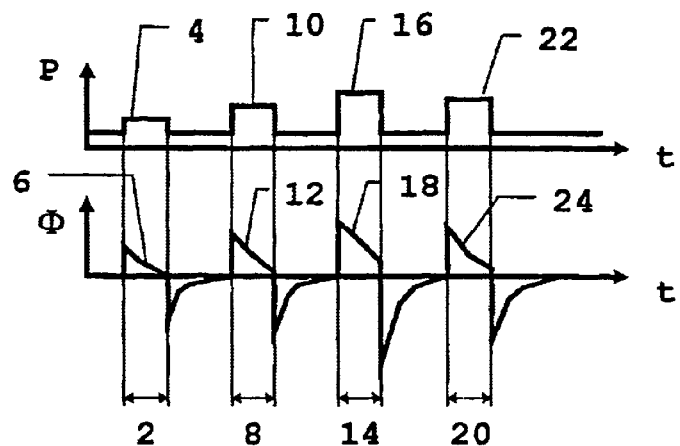
FIG. 1 shows flow and pressure patterns for the known volume support (VS) breathing mode.

As noted above, FIG. 1 shows pressure and flow patterns for the known volume support (VS) breathing mode. An improvement in this operating mode is achieved according to the present invention when compensation is provided for resistances in the apparatus and tubing and for variations in resistance and elastance occurring in a patient's lungs and airways.

Figure 2:
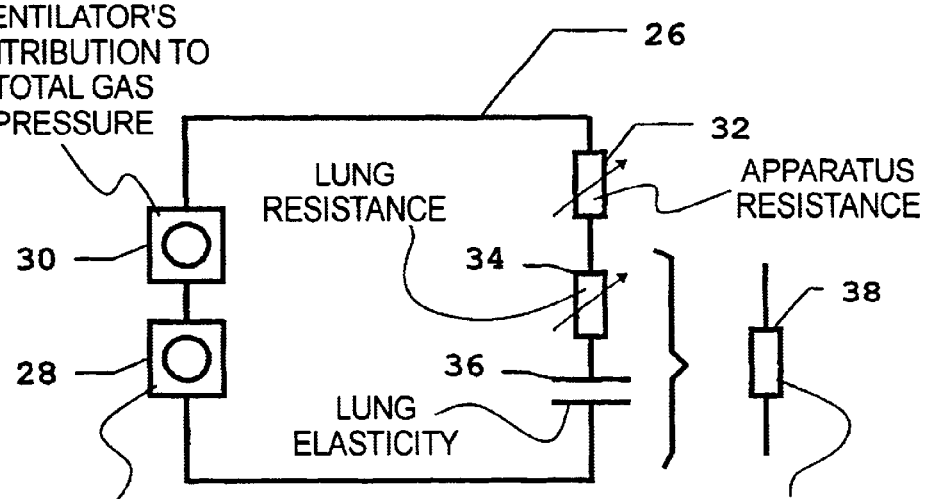
FIG. 2 shows a model of a breathing system and ventilator in the form of a circuit diagram.

This is schematically illustrated in FIG. 2 with a circuit diagram 26. Here, an analogy is made with electrical components and terminology. A first power source 28 designates the gas pressure the patient's muscular efforts are capable of generating, and a second power source 30 designates the ventilator's contribution to total gas pressure (the power sources accordingly correspond to sources of voltage in an electrical circuit.)

In this circuit diagram 26, a first resistance 32 designates apparatus resistance, in particular resistance to flow in a tracheal tube connected to the patient. As a rule, the first resistance 32 is variable, since changes in the position of the tracheal tube and tubing have an effect on resistance to flow.

A second resistance 34 and a capacitance 36 correspond to the resistance to flow and elasticity of the patient's lungs respectively. Both the second resistance 34 and the capacitance 36 are variable. The second resistance 34 and the capacitance 36 can be aggregated to form a (variable) impedance 38.

A number of advantages are achieved when the impedance 38 is allowed to be a variable in determinations of the ventilator's contribution (the second source of power 30) to gas pressure during inspiration.

The ventilator's contribution to gas pressure can adapt more rapidly to changes in the patient's condition (both improvement and worsening) than a ventilator operating according to known breathing modes. This makes control of the ventilator more stable, and the risks otherwise associated with positive feedback are minimized. This also means that the ventilator does not need to be constantly monitored by qualified medical staff.

Since the ventilator's contribution is not fixed, as in PAV, the patient's and ventilator's respective contributions to breathing work can be determined and viewed on a display (or the equivalent) by medical staff. Such a presentation can be graphical or numerical (e.g. the patient's contribution in form of a percentage number). Over time this distribution supplies important information on the patient's condition, especially tendencies indicative of improvement in or worsening of the patient's condition. Trend data showing such changes can also be presented on the display.

This new operating mode also results in a predictable level of carbon dioxide for the patient, since gas delivery is more predictable in other adaptive breathing modes such as PAV.

Figure 3:
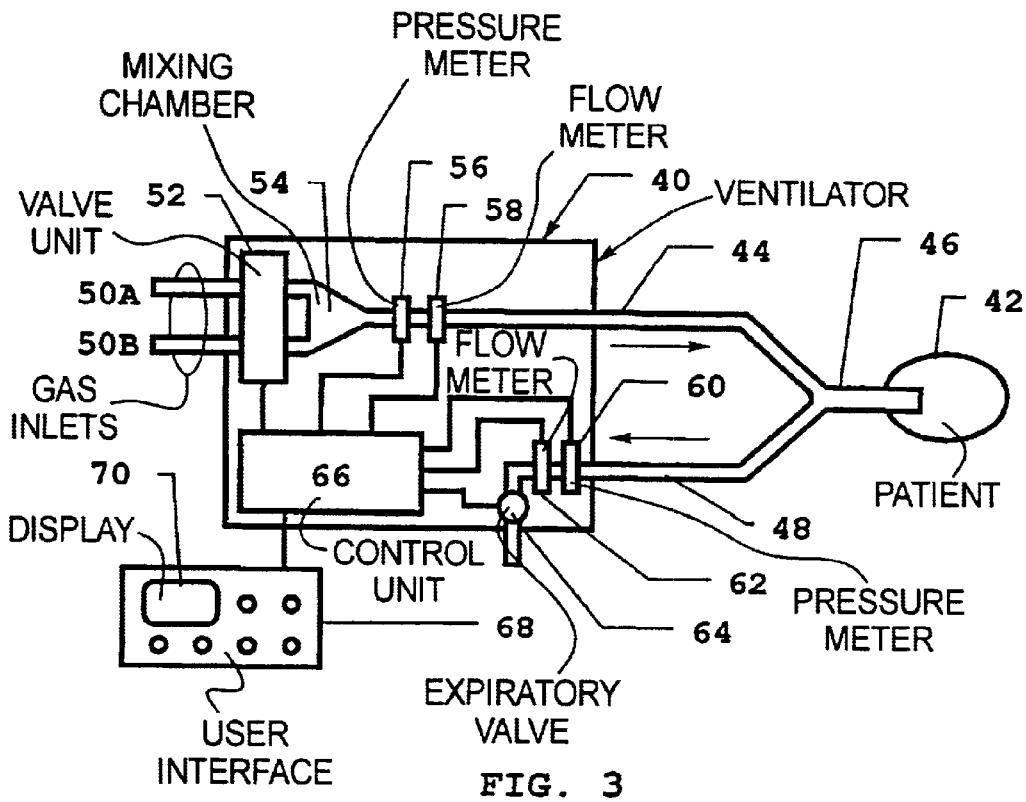
FIG. 3 shows an embodiment of a ventilator according to the invention.

FIG. 3 shows an embodiment of a ventilator 40 according to the invention. The ventilator 40 is connected to a patient 42 by a system of tubing consisting of an inspiratory tube 44, a patient tube 46 (primarily a tracheal tube) and an expiratory tube 48.

Different gases can be connected to the ventilator 40 through a first gas inlet 50A and a second gas inlet 50B. The pressure and flow of supplied gases are regulated by a valve unit 52, and the gases are then mixed into a breathing gas in a chamber 54. During inspiration, breathing gas is sent to the inspiratory line 44 for delivery to the patient 42. A first pressure meter 56 and a first flow meter 58 also can be arranged in the flow path up to the inspiratory line 44.

During expiration, expired breathing gas and any bias flow of gas from the ventilator 40 are carried through the expiratory line 48 back to the ventilator 40. A second pressure meter 60 and a second flow meter 62 are arranged in this flow path. An expiratory valve 64 regulates the discharge of gas into atmosphere (or into an evacuation unit). The expiratory valve 64 can e.g. be controlled to maintain a specific end pressure after each completed exhalation, i.e. a positive end expiratory pressure (PEEP).

A control unit 66 controls and monitors all functions in the ventilator 40. The operating mode and reference values for the operating mode can be set on a user interface 68. Other information of interest, such as the patient's weight, the diagnosis, the type of tubing (the tracheal tube in particular) etc., can also be entered via the user interface 68. The reference values, actual values and different event sequences during breathing cycles can be presented on a display (monitor) 70.

The control unit 66 is designed to control the valve unit 52 and the expiratory valve 64 so the selected operating mode is maintained with the programmed parameters, e.g. pressure, PEEP, breathing rate, tidal volume, minute volume, inspiratory duration, triggering level etc.

More specifically, the control unit 66 is devised to control at least the ventilator 40 according to the aforementioned modified volume support mode, viz, compensated volume support (CVS).

As shown in the above-described circuit diagram for the model used, the following equation can be set up for the required pressure contribution event made by the ventilator:

$$P_{vent} = (R_{app} * V' + I_{pat} * V) - P_{pat}$$

in which $R_{app}$ is apparatus resistance (the tracheal tube in particular), $V'$ is flow through the tubing (the tracheal tube in particular), $I_{pat}$ is the patient's aggregate elastance and resistance, V is tidal volume and $P_{pat}$ is the pressure the patient is capable of generating. Apparatus resistance $R_{app}$ can be determined e.g. by calculations based on geometric conditions or in some other appropriate fashion. The flow $V'$ can be measured with a flow meter. Patient pressure $P_{pat}$ can be measured with a pressure meter. Tidal volume V is entered as the target value to be achieved. Determination of $P_{vent}$ can be made explicitly in every breathing cycle or as the result of an error function over a number of breathing cycles.

Figure 4:
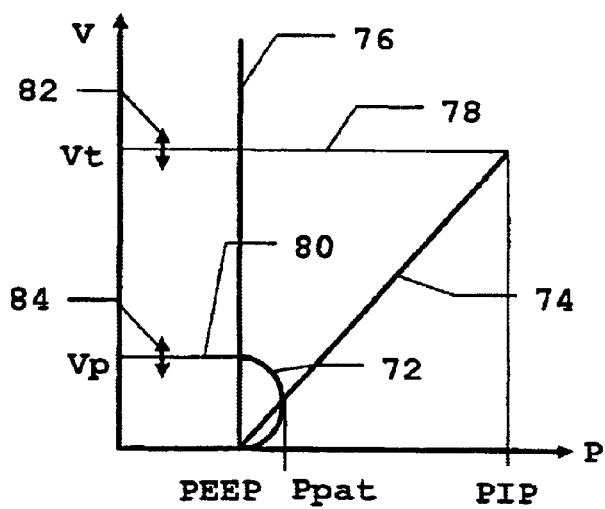
FIG. 4 is a pressure-flow diagram of one breathing cycle using the inventive ventilator.

A particular advantage of the inventive operation mode is evident from FIG. 4, which shows one breath in a volume-pressure diagram (using the parameters as defined in the above equation). A first curve 72 shows the patient's breathing capacity, and a second curve 74 shows the ventilator's contribution to breathing. The patient is capable of generating the pressure $P_{pat}$ above PEEP (indicated as a vertical line in the diagram) and receives assistance from the ventilator in reaching the volume Vt (this assistance consisting of $P_{vent}$).

The pressure PIP is necessary for achieving the tidal volume Vt (entered as a first horizontal line 78 in the diagram) Without breathing assistance contributed by the ventilator, the patient would only achieve the volume/breath designated as Vp (indicated as a second horizontal line 80 in the diagram). The two volumes, i.e. Vt, Vp, have been designated as variables with the arrows 82, 84.

On the basis of this diagram, the breathing contributions made by the patient and ventilator respectively can be determined and entered on the display. This can e.g. be performed with graphic display of the diagram or by having the control unit calculate the respective contributions and displaying them, e.g. 25% by the patient and 75% by the ventilator. In addition, trend data showing the changes in the respective contributions over time can also be displayed.

Detailed realization of the control unit can be achieved with hardware, software or any combination thereof.

Although modifications and changes may be suggested by those skilled in the art, it is the intention of the inventor to embody within the patent warranted hereon all changes and modifications as reasonably and properly come within the scope of his contribution to the art.

I claim as my invention:

1. A ventilator comprising:

a gas flow generator which produces a flow of gas in a gas flow path in a conduit system adapted for communication with a patient having lungs exhibiting a resistance and an elasticity, said conduit system comprising a plurality of components disposed in said gas flow path having respective mechanical resistances to said flow of gas;

a pressure meter which measures pressure in said conduit system and which produces a pressure measurement signal dependent thereon;

a flow meter which measures gas flow in said conduit system and which produces a flow measurement signal dependent thereon;

a control unit having an input for setting a predetermined tidal volume, and which receives said pressure measurement signal and said flow measurement signal, and which determines a gas pressure, in each breathing cycle of a patient, from said tidal volume, said pressure measurement signal, said flow measurement signal, and a variable representing an aggregate effect of said resistance and elasticity of the lungs, said control unit programmed to regulated said gas flow generator to cause said gas flow generator to generate said gas flow at the gas pressure respectively determined for that breathing cycle.

2. A ventilator as claimed in claim 1 wherein said conduit system includes a tracheal tube, and wherein said mechanical resistances comprise resistance to gas flow in said tracheal tube.

3. A ventilator as claimed in claim 1 further comprising a display connected to said control unit.

4. A ventilator as claimed in claim 3 wherein said control unit identifies parameters relating to mechanical breathing support for each breath, said parameters being shown on said display.

5. A ventilator as claimed in claim 4 wherein said control unit determines trend changes in said breathing support over time, and displays said trend changes on said display.

6. A ventilator as claimed in claim 3 wherein said control unit calculates parameters relating to breathing activity of a patient in each breath, said control unit displaying said parameters on said display.

7. A ventilator as claimed in claim 6 wherein said control unit determines trend changes in said breathing support over time, and displays said trend changes on said display.

8. A ventilator as claimed in claim 1 wherein said conduit system includes an inspiratory line adapted to supply gas from said gas flow generator to a patient, and wherein said pressure meter measures pressure in said inspiratory line and said flow meter measures gas flow in said inspiratory line.

9. A ventilator as claimed in claim 1 wherein said conduit system includes an expiratory line, adapted to receive gas from a patient, and wherein said pressure meter measures pressure in said expiratory line and said flow meter measures gas flow in said expiratory line.

10. A ventilator as claimed in claim 1 wherein said control unit determines said gas pressure from said tidal volume, said pressure measurement signal, said flow measurement signal, said variable, and said mechanical resistances.

\* \* \* \* \*